US008691769B2

(12) United States Patent
Borodic et al.

(10) Patent No.: US 8,691,769 B2
(45) Date of Patent: Apr. 8, 2014

(54) TREATMENT OF SINUSITIS RELATED CHRONIC FACIAL PAIN AND HEADACHE WITH BOTULINUM TOXIN INJECTIONS

(75) Inventors: Gary Borodic, Canton, MA (US); Martin Andrew Acquadro, Wellesly, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 1264 days.

(21) Appl. No.: 10/793,964

(22) Filed: Mar. 8, 2004

(65) Prior Publication Data

US 2004/0247606 A1 Dec. 9, 2004

Related U.S. Application Data

(60) Provisional application No. 60/453,037, filed on Mar. 6, 2003.

(51) Int. Cl.
*C07K 14/33* (2006.01)
*A61K 38/16* (2006.01)

(52) U.S. Cl.
USPC .......................................................... 514/18.3

(58) Field of Classification Search
None
See application file for complete search history.

(56) References Cited

U.S. PATENT DOCUMENTS

| | | | |
|---|---|---|---|
| 4,940,728 A * | 7/1990 | Postley | 514/474 |
| 5,437,291 A | 8/1995 | Pasricha et al. | |
| 5,512,547 A | 4/1996 | Johnson et al. | |
| 5,562,908 A * | 10/1996 | Geria | 424/434 |
| 5,576,468 A | 11/1996 | Lubowitz | |
| 5,670,484 A | 9/1997 | Binder | |
| 5,674,205 A | 10/1997 | Pasricha et al. | |
| 5,696,077 A | 12/1997 | Johnson et al. | |
| 5,714,468 A | 2/1998 | Binder | |
| 5,766,605 A | 6/1998 | Sanders et al. | |
| 5,846,929 A | 12/1998 | Johnson et al. | |
| 5,989,545 A | 11/1999 | Foster et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,265,379 B1 | 7/2001 | Donovan | |
| 6,299,893 B1 | 10/2001 | Schwartz et al. | |
| 6,306,403 B1 | 10/2001 | Donovan | |
| 6,306,423 B1 | 10/2001 | Donovan et al. | |
| 6,312,706 B1 | 11/2001 | Lai et al. | |
| 6,312,708 B1 | 11/2001 | Donovan | |
| 6,328,977 B1 | 12/2001 | Donovan | |
| 6,358,513 B1 | 3/2002 | Voet et al. | |
| 6,365,164 B1 | 4/2002 | Schmidt | |
| 6,395,277 B1 | 5/2002 | Graham | |
| 6,423,319 B1 | 7/2002 | Brooks et al. | |
| 6,429,189 B1 | 8/2002 | Borodic | |
| 6,458,365 B1 | 10/2002 | Aoki et al. | |
| 6,464,986 B1 * | 10/2002 | Aoki et al. | 424/239.1 |
| 6,838,434 B2 * | 1/2005 | Voet | 514/2 |
| 6,869,610 B2 | 3/2005 | Aoki et al. | |
| 7,537,773 B1 * | 5/2009 | Borodic | 424/282.1 |
| 2001/0036943 A1 * | 11/2001 | Coe et al. | |
| 2002/0036943 A1 | 3/2002 | Fujimoto | |
| 2002/0187164 A1 | 12/2002 | Borodic | |
| 2002/0192239 A1 | 12/2002 | Borodic et al. | |
| 2002/0197278 A1 | 12/2002 | Allison | |
| 2002/0197279 A1 | 12/2002 | Aoki et al. | |
| 2003/0138437 A1 | 7/2003 | Hunt | |
| 2003/0143249 A1 | 7/2003 | Lamb | |
| 2004/0126396 A1 | 7/2004 | Aoki et al. | |
| 2004/0138097 A1 * | 7/2004 | Guyuron | |
| 2006/0008462 A1 * | 1/2006 | Sanders | 424/184.1 |

FOREIGN PATENT DOCUMENTS

WO WO 02/07759 * 1/2002 ............. A61K 38/48

OTHER PUBLICATIONS

Bergogne-Bérézin 2002. Expert Opin. Pharmacother. 3:1471-1479.*
Borodic 2001. Expert Opin. Investig. Drugs 10:1531-1544.*
Whittet 1992. Otolaryngol Head Neck Surg 107:21-28.*
Walker 1990 (Cranial Nerve V: The Trigeminal Nerve, Chapter 61 in Clinical Methods, Third Edition).*
Acquadro 1996 (Ann Otol Rhinol Laryngol 105:607-614).*
Close 1997 (Seminars in Neurology 17(4):351-354).*
Anderson, T. et al., "Surgical Intervention for Sinusitis in Adults," Current Allergy and Asthma Reports, 2001, 1:282-288.
Aoki, K.R. et al., "Botulinum toxin type A and other botulinum toxin serotypes: a comparative review of biochemical and pharmacological actions," European Journal of Neurology 2001, 8 (Suppl.5): 21-29.
Aoki, K.R., "Physiology and Pharmacology of Therapeutic Botulinum Neurotoxins," Curr Probl Dermatol. Basel, Karger, 2002, vol. 30, p. 107-116.
Bigalke, Hans et al., "Botulinum A Neurotoxin Inhibits Non-Cholinergic Synaptic Transmission in Mouse Spinal Cord Neurons in Culture," Brain Research, 360 (1985) 318-324.
Bigalke, Hans et al., "Tetanus Toxin and Botulinum A Toxin Inhibit Release and Uptake of Various Transmitters, as Studied with Particulate Preparations from Rat Brain and Spinal Cord," Naunyn-Schmiedeberg's Arch Pharmacol (1981) 316: 244-251.
Binz, Thomas et al., "the Complete Sequence of Botulinum Neurotoxin Type A and Comparison with Other Clostridial Neurotoxins." The Journal of Biological Chemistry, vol. 265, No. 16, Issue of Jun. 5, pp. 9153-9158, 1990.
Borodic et al., "Management of Facial Pain with Botulinum Toxin in a Tertiary Pain Clinic," Naunyn Schmiedebergs Arch Pharmacol, 2002; 365 (Suppl 2):R14.
Brem, Henry et al., "Placebo-controlled trial of safety and efficacy of intraoperative controlled delivery by biodegradable polymers of chemotherapy for recurrent gliomas," The Lancet, vol. 345, Apr. 22, 1995; pp. 1008-1012.

(Continued)

*Primary Examiner* — Daniel E Kolker
(74) *Attorney, Agent, or Firm* — Milbank Tweed Hadley & McCloy LLP

(57) ABSTRACT

The present invention provides methods for treating sinus-evoked headaches using botulinum toxin injected or applied in multiple subcutaneous locations over divisions of the trigeminal nerve in soft tissues and dermatomes overlying the corresponding effected sinuses implicated in the etiology of the pain.

32 Claims, 2 Drawing Sheets

(56) References Cited

OTHER PUBLICATIONS

Bushara, K.O. et al., Botulinum Toxin and Rhinorrhea, Otolaryngol Head Neck Surg; 1996; 114 (3): 507.
Cui, M. et al., "Mechanisms of the Antinociceptive Effect of Subcutaneous Botox: Inhibition of Peripheral and Central Nociceptive Processing," Naunyn Schmiedebergs Arch Pharmacol; 2002; 365 (Suppl 2) R17; Abstract.
Moyer, Elizabeth et al., "Botulinum Toxin Type B: Experimental and Clinical Experience," In: Jankovic J, ed. Neurological Disease and Therapy. Therapy with Botulinum Toxin; 1994; 25; pp. 71-85.
Naumann, Markus et al., Botulinum toxin type A in the treatment of focal, axillary and palmar hyperhidrosis and other hyperhidrotic conditions,: European Journal of Neurology 1999, 6 (suppl 4): S111-5115.
Pearce, L. Bruce et al., "Pharmacologic Characterization of Botulinum Toxin for Basic Science and Medicine," Toxicon; 1997; 35(9); pp. 1373-1412.
Ragona, Rosario M. et al., "Management of Paratoid Sialocele with Botulinum Toxin," Laryngoscope; 109; Aug. 1999 (8); pp. 1344-1346.
Rollnik, J.D. et al., "Botulinum Toxin (DYSPORT) in Tension-Type Headaches," Acta Neurochir, 2002; 79 (suppl): 123-126.
Rohrbach, S. et al., "Minimally Invasive Application of Botulinum Toxin Type A in Nasal Hypersecretion," J Oto-Rhino-Laryngol Nov.-Dec. 2001, 63(6):382-4.
Sanchez-Prieto, Jose et al., "Botulinum toxin A blocks glutamate exocytosis from guinea-pig cerebral cortical synaptosomes," Eur. J. Biochem. 165, 675-681 (1987).
Schantz, Edward J. et al., "Properties and Use of Botulinum Toxin and Other Microbial Neurotoxins in Medicine," Microbiological Reviews, Mar. 1992, p. 80-99.
Singh, Bal Ram, "Critical Aspects of Bacterial Protein Toxins," Natural Toxins II; Edited by B.R. Singh et al., Plenum Press, New York, 1996; Chapter 4, pp. 63-84.
Sloop, R. Richard et al., "Reconstituted botulinum toxin type A does not lose potency in humans if it is refrozen or refrigerated for 2 weeks before use," Neurology; Jan. 1997; 48(1): 249-53.
Thant, Zin-Soe et al., "Emerging therapeutic applications of botulinum toxin," Med Sci Monit 2003; 9(2): RA40-48.
Wiegand, H. et al., "I-Labelled Botulinum A Neurotoxin: Pharmacokinetics in Cats after Intramuscular Injection," Naunyn Schmiedeberg's Arch. Pharmacol. 292, 161-165 (1976).
"Headache, A Patient Guide," PDF file from website www.imigraine.net/patient/guide.pdf on Mar. 13, 2003, Wake Forest University Baptist Med Center, Dept. of Neurology.
Duggan, Michael J. et al. "A survey of botulinum neurotoxin substrate expression in cells," Mov Disord; May 1995; 10(3) p. 376.

Evers, S. et al., "Treatment of headache with botulinum toxin A—a review according to evidence-based medicine criteria," Cephalalgia Nov. 2002; 22(9): 699-710.
Ferrari, David M. et al., "The protein disulphide-isomerase family: unravelling a string of folds," Biochem J; 1999 (339) pp. 1-10.
Freund, Brian J. et al., "The use of Botulinum toxin-A in the treatment of refractory cluster headache: case reports," Cephalagia 2000; 20(4): 329-330.
Freund, B.J. et al., "Relief of Tension-type Headache Symptoms in Subjects with Temporomandibular Disorders Treated with Botulinum Toxin-A," Headache Nov.-Dec. 2002; 42(10)1033-1037.
Freund, Brian J. et al., "Treatment of Chronic Cervical-Associated Headache With Botulinum Toxin A: A Pilot Study," Headache Mar. 2000; 40(3):231-236.
Fung, Lawrence K. et al.. "Pharmacokinetics of Interstitial Delivery of Carmustine, 4- Hydroperoxycyclophosphamide, and Paclitaxel from a Biodegradable Polymer Implant in the Monkey Brain," Cancer Research; 58, Feb. 15, 1998: pp. 672-684.
Habermann, E., "125I-Labeled Neurotoxin from Clostridium Botulinum A: Preparation, Binding to Synaptosomes and Ascent to the Spinal Cord," Naunyn-Schmiedeberg's Arch. Pharmacol. 281, 47-56 (1974).
Habermann. E., "Inhibition by tetanus and botulinum A toxin of the release of [3H]noradrenaline and [3H]GABA from rat brain homogenate," Experienta: Mar. 15, 1988; 44 (3) pp. 224-226.
Habermann, Ernst et al., "Tetanus Toxin and Botulinum A and C Neurotoxins Inhibit Noradrenaline Release from Cultured Mouse Brain," Journal of Neurochemistry; vol. 51, No. 2 1988; pp. 522-527.
Loder, Elizabeth et al., "Use of Botulinum Toxins for Chronic Headaches: A Focused Review," The Clinical Journal of Pain 2002; 18 (6 suppl): S169-S176.
Marjama-Lyons, J. et al., "Tremor-Predominant Parkinson's Disease," Drugs & Aging; Apr. 16, 2000; (4); 273-278.
Mathew, N.T. et al., "The Use of Botulinum Toxin Type A in Headache Treatment," Curr Treat Options Neurol Sep. 2002; 4(5): 365-373.
Acquadro, Martin A. et al. "Treatment of Myofascial Pain with Botulinum A Toxin," Anesthesiology, vol. 80, No. 3, Mar. 1994.
Shaari et al., "Rhinorrhea is decreased in dogs after nasal application of botulinum toxin," Otolaryngology, Head and Neck Surgery, Apr. 1995, XP-002976784.
C.P.N. Watson et al., Post-herpetic neuralgia: further post-mortem studies of cases with and without paint, Pain, 44 (1991) 105-117.
Understanding Postherpetic Neuralgia—the Basics, Shingles Heal Center, The Basics of Postherpetic Neuralgia, pp. 1-2, printed Sep. 16, 2010.
S. L, Robbins, "Pathologic Basis of Disease", pp. 72, 102-103, 1471.
Concentrations of substance P and prostaglandin E2 in synovial fluid of normal and abnoral joint of horses, Abstract, American Journal of Veterinary Research, Jun. 2000, vol. 61, No. 6, pp. 714-718.

\* cited by examiner

TREATMENT OF SINUSITIS RELATED CHRONIC FACIAL PAIN AND HEADACHE WITH BOTULINUM TOXIN INJECTIONS

This application claims benefit to U.S. Provisional Application Ser. No. 60/453,037 that was filed on Mar. 3, 2003.

TECHNICAL FIELD OF THE INVENTION

This invention relates to methods for treating headache and facial pain associated with acute recurrent or chronic sinusitis with botulinum toxin.

BACKGROUND OF INVENTION

Botulinum neurotoxin, a toxin isolated from a strain of *Clostridium botulinum*, a deadly toxin at higher concentrations and quantities, has been used as a valuable therapeutic for the treatment of many neuromuscular diseases (e.g., dystonia, hemifacial spasm, bruxism, spasticity, cerebral palsy, torticollis), as well as sensory disorders and cutaneous disorders (myofacial pain, migraine, tension headaches, neuropathy, hyperhydrosis). Although botulinum toxin has been used for the treatment of migraine and tension headaches, botulinum toxin has not been recognized as an effective therapy for headache and facial pain associated with acute recurrent or chronic sinusitis.

Sinus-related headaches are distinctly different from migraine headache, myofascial headaches, and headaches associated with bruxism, temporal mandibular joint syndrome (TMJ) and temporal mandibular muscle dysfunction (TMD), trigeminal neuralgia, tooth related facial pain, pain associated with elevated intraocular pressure, or internal ocular inflammation. Sinus headaches are associated with pressure, or irritating processes within the sinus cavities, sometimes associated with inflammation and impaired flow of mucous secretion. At some point in the diagnostic workup, excessive signs of inflammation within the sinus or nasal cavity, or edema within the sinus or nasal cavity is demonstrated on exam or via radiographic methods. The present inventors have discovered that botulinum toxin relieves the headache and facial pain associated with sinusitis.

SUMMARY OF THE INVENTION

The present invention provides methods of treating headache and facial pain associated with acute recurrent or chronic sinusitis in a subject in need thereof, comprising the step of administering a therapeutically effective amount of a composition comprising botulinum toxin to the nasal mucosa or to the subcutaneous structures overlaying the sinuses, wherein the administration of the composition reduces the headache and facial pain associated with acute recurrent or chronic sinusitis. In a preferred embodiment, the sinuses are one or more of the sinuses selected from the group consisting of: ethmoid; maxillary; mastoid; frontal; and sphenoid. Preferably, the subcutaneous structures overlaying the sinuses lie within one or more of the areas selected from the group consisting of: forehead; malar; temporal; post auricular; and lip.

Botulinum toxin may be administered to the nasal mucosa or to the subcutaneous structures overlaying the sinuses by any number of methods. Preferably, the composition comprising botulinum toxin is administered by injection at one or more injection sites. More preferably, the composition comprising botulinum toxin is administered to the cutaneous projections of the trigeminal nerve innervating the sinus.

In one embodiment of the present invention, a subject is treated by administration of a composition comprising botulinum toxin, wherein the subject, prior to the onset of facial pain or headache, exhibits symptoms or history of sinus rhinorrhea (nasal hypersecretion) and purulent nasal discharge.

The methods of the present invention may be practiced with various botulinum toxin immunotypes. In one embodiment, the botulinum toxin is any one or more botulinum toxin immunotypes selected from the group consisting of: A; B; C; D; E; F; and G. Furthermore, the methods of the present invention may utilize compositions of botulinum toxin wherein the composition is administered at a dose between 0.5 and 50,000 mouse $LD_{50}$ units of botulinum toxin. In a preferred embodiment, between 15 and 200 mouse $LD_{50}$ units spread over multiple injections within a dermatome corresponding to the sinus sensory innervation.

DETAILED DESCRIPTION OF INVENTION

A. Definitions

Figure 1:
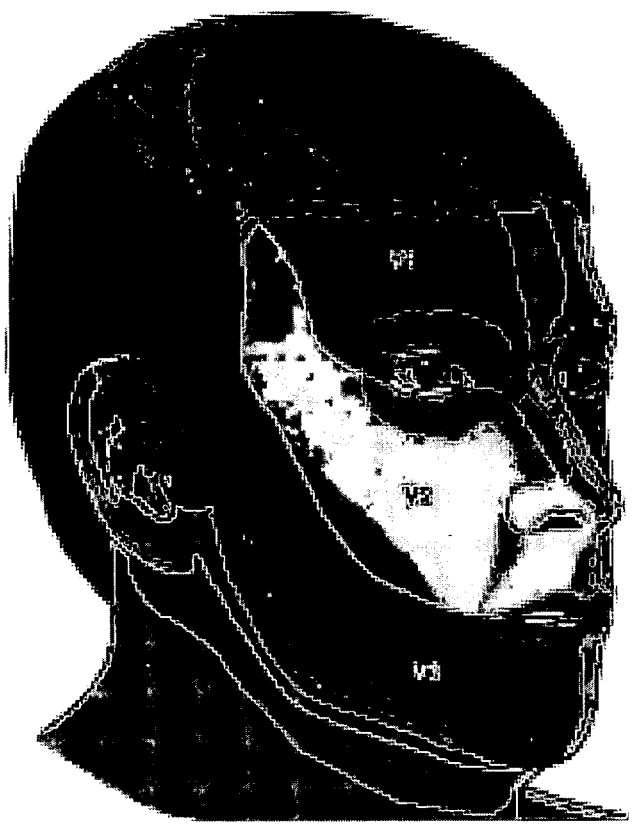
FIG. 1 shows the projection of the trigeminal nerve both to the sinuses and the cutaneous and soft tissue structures of the face.

As used herein, "Botulinum toxin" means a protein toxin and its complexes isolated from strains of *Clostridium botulinum*, including various immunotypes such as A, B, C1, C2, C3, D, E, F and G.

As used herein, "a therapeutically effective amount" is an amount sufficient to produce a therapeutic response. An effective amount may be determined with dose escalation studies in open-labeled clinical trials or bin studies with blinded trials.

As used herein, "subject" means a mammal.

B. Sinusitis

Sinusitis is defined as any inflammatory pathology involving the ethmoid, maxillary, frontal, or sphenoid sinuses. It is generally accepted that the cause of pain occurring with acute sinusitis involves infiltration of sinus mucosa with inflammatory cells, as well as increased pressure within the sinuses. What is generally not appreciated, and is herein disclosed, is that sinusitis can cause sensitization of the trigeminal nerve in cutaneous and subcutaneous tissues overlaying the sinus structures. When sensitization of sensory nerves occurs from repeated bouts of sinusitis, the patient can experience a chronic facial pain syndrome or headache. The mechanism by which sensory nerves become up-regulated or sensitized still is not clear. Nerve sensitization is provoked by alterations in the afferent first-order-sensory nervous system, such that thresholds are lowered to the perception of pain (hyperalgesia) and central second-order or higher-neuronal alterations can occur, resulting in an exaggerated response and interpretation of sensory stimuli (central sensitization). This process has been experimentally associated with increased expression and/or responsiveness of NMDA receptors on membranes of nociceptors and possible alterations in transcription and translation of proteins within the nerve cell. The trigeminal ganglia represent a very large collection of afferent sensory neurons, which send projects not only into cutaneous regions of the head, but also internally into osseous sinus structures, and mucous membranes of the nasal and sinus cavities (see FIG. 2). The arborization pattern of afferent sensory nerve distribution is extensive, but reactivity within any region of the afferent sensory nerve distribution has the capability of altering the genetic and cellular-protein expression of the sensory nerve cell body within the ganglion. The process of changing cell physiology has been variously coined neuroplasticity or sensitization. Alterations can be in the form of increased expression of nerve cell receptors, such as AMPA and NMDA receptors, modulation of effectors of inflammation, alteration of cellular responses from blood-vessel neural regulation via nitric oxide, substance P, histamine, CRGP, prostaglandins, other known cellular autocoids, and not yet defined autocoids and neuropeptides. The mechanism for sensitization of human nerve cells is still not well understood, and invoking inflammatory mediators, neurogenic inflammatory autocoids, and transcriptional and phenotypic changes of nociceptors and sensory neurons as the only mechanisms for nerve sensitization is not necessary to elicit responses from therapeutic botulinum toxin for this indication. Sensitization in the periphery is thought to occur following a sufficient or prolonged exposure to inflammatory substances, causing altered physiology, possible conformational changes of certain biochemical receptors, responsiveness, and lowered thresholds for nociceptor and sensory nerve depolarization.

Sinus pain usually begins in the mid facial region over the maxillary sinus and can radiate to temporal regions, ocular regions, vertex, and over the forehead. At times, referred pain can project into the posterior cervical region or peri-auricular areas. Generalized headaches can occur. The trigeminal nucleus is somatotropically well organized, and from the brain stem area, directly extends and connects anatomically to the upper-cervical areas of the dorsal horn of the spinal cord. In addition, there are interneuronal connections between the trigeminal nucleus and other cranial nerve nuclei, the autonomic nervous system, the reticular activating system, and other descending and ascending pathways. This interconnecting system has been described as the trigeminal sensory complex. Since there are many more peripheral upper cervical and trigeminal sensory nerves synapsing on fewer central nerves, this has been described as convergence and projection. This can explain the referral patterns of head and neck pains, and the therapies employed in one area of the head and neck to affect an outcome on a another area of the head and neck with shared and referred sensory pathways.

Distinct differences in headache diagnosis have been formulated at international conventions and remain the basis for both general and research practice. For migraine headaches, the presence of episodic headaches lasting 4-48 hrs, associated with light sensitivity (photophobia), sound sensitivity (phonophobia), nausea or vomiting, pain of a throbbing or pulsating quality, and more often unilateral than bilateral location of headache. Cluster headaches can be associated with some basal transient nasal congestion but occur over a distinct time period (cluster period) and are not associated with any persistent sinus abnormalities on MRI or computerized tomography. Myofascial and tension headaches often have a cap-like squeezing pain across and around the top of the head, often associated with a cervical musculoskeletal pain location, frequently associated with trigger points, and sometimes associated with decreased jaw motility and bruxism if the masseter and temporalis muscles are involved. Ocular-related headaches are associated with increased intraocular pressure or signs of intra-ocular inflammation on slit lamp microscopic exam or measured refractive error. Dental-related headaches are associated with findings on dental examination and radiographs. Trigeminal neuralgia is usually limited to one or two dermatomes and is sharp and stabbing in quality, with a rapid "on-off" episodic pattern sometimes associated with stimulation of trigger points.

Chronic-sinusitis-related headache and facial pain can linger for many months to years after an acute or subacute bout of sinus disease or bout of repeated acute sinus headaches. Often, the patient complains of continued pain when radiologic imaging studies, such as computerized tomography and magnetic resonance imaging fail to show any persisting signs of inflammation such as mucosal thickening or fluid accumulation. Often out of desperation, the surgeon performs decompressive surgery via endoscopes or direct approaches (Culdwell luc, external ethmoidectomy) with poor results with respect to the chronic pain. The above observation explains a very common clinical phenomenon associated with chronic facial pain and headache caused by sinusitis. The reason for the persisting pain despite the absence of active sinus findings is peripheral sensory nerve upregulation or sensitization. Direct treatment of sinus-related headache by botulinum toxin injected into the subcutaneous region to down-regulate sensory nerves is therapeutic.

The convention in treating sinus-related headaches involves decongestants to augment mucous clearance and drainage from sinus cavities, antibiotics to treat bacterial infection, anti-inflammatory medication (e.g. corticosteroids), and surgical decompression. Conventional analgesics such as aspirin and acetaminophen may be used. The present inventors have made the unexpected discovery that administration of botulinum toxin over the surface dermatomes containing the sensory branches corresponding to the neurons projecting into the sinus cavity effectively treats facial and headache pain associated with sinusitis.

C. Formal Classification and Nosology of Sinus Related Head and Neck Pain

A convention held in 1985 by the International Headache Society (I.H.S.) put forth an exhaustive classification of distinct headache syndromes. Experts in the headache therapeutic field formulated this classification, and such experts explicitly agreed on the importance of headache distinction both for practice and research. The reasons for distinctions are to promote better communication among practitioners and to provide more exacting therapy for specific headache syndromes. For instance, procedures used to treat trigeminal neuralgia, such as glycerol injections, gamma knife application, and microvascular decompression at the level of the brainstem are not effective for the treatment of recurrent sinus headache. Tryptin-related pharmaceuticals (e.g. Imitrex™, Zomig™)) would be ineffective for the treatment of sinus headache and laser iridectomy for the treatment of narrow angle glaucoma would be ineffective for the treatment of migraine. Cluster headache needs to be distinguished from migraine. Hence, one skilled in the art of treatment of pain would require specific and professionally acceptable diagnosis in order to recommend reasonable therapy or to conduct clinical trials with potentially effective new therapies. The convention held in 1985 and subsequently published in Cephalgia (1988 Vol 8 (supplement 7), 1-96) has served as a benchmark for diagnosis and classification of human headaches (nosology) for the past 15 years.

In order for the physician to function and recommend therapeutic interaction with patients suffering from pain, classification with diagnostic criteria of an affliction must be determined. Classification of disease must be operationally specified with quantitative parameters and not just descriptive. The International Headache Society (I.H.S.) formed a committee in 1995 which lead to the first adopted international headache classification, which in turn permitted uniform operational criteria for diagnosis. The I.H.S. is internationally accepted and has been incorporated into the World Health Organization (W.H.O.) classification of disease. This classification has been translated into multiple languages and competes with no other classification system (see Jes Olesen Classification of Headache in Chapter 2, The Headaches, $2^{nd}$ Edition, Lippincott, Williams and Wilkins ed Olesen, Hansen, Walsh, Philadelphia, 1999). An outline of the operational classification system is presented in Table 1.

In the classification system, headaches in category 1-4 are primary headache disorders with no associated anatomic pathologic process. Groups 5-11 are headaches and cervical pain associated with some other demonstrable disease process (trauma, vascular disease, increased intracranial pressure, withdrawal from substances, systemic infection, metabolic disorder, eye, ear, nose, and throat disease, or dental disease. Group 12 relates to cranial neuralgias.

The classification is quantitative, which allows for specific diagnosis. An excellent example of operation of the classification can be noted with the diagnosis of common migraine:

I.H.S. Classification 1.1 (Migraine without Aura—Common Migraine)

Diagnostic criteria for migraine without aura:
A. At least 5 attacks fulfilling B-D.
B. Headache attacks lasting 4-72 hours.
C. Headache has at least two of the following characteristics:
  1. Unilateral location.
  2. Pulsating quality.
  3. Moderate to severe intensity (inhibits or prohibits daily activities).
  4. Aggravation by walking stairs or similar routine physical activity.
D. During headache, at least one of the following:
  1. Nausea and for vomiting.
  2. Photobobia and/or phonophobia.
E. At least one of the following:
  1. History and/or physical and/or neurological examinations do not suggest any one of the disorders listed in groups 5-11.
  2. History and/or physical and/or neurological examinations do suggests any one of the disorders listed in groups 5-11, but it is ruled out by appropriate investigations.
  3. Such a disorder (groups 5-11) is present, but migraine attacks do not occur for the first time in close temporal relationship to the disorder.

The I.H.S. classification of common migraine presented above is the method most reliably used for the diagnosis of migraine headaches and has been used in large multi-centered multinational double blinded drug trials used in the investigation of triptan based drugs for treatment of migraine (The Subcutaneous Sumatriptan International Study Group. Treatment of Migraine Attacks with Sumatriptan. N Engl J Med 1991:325: 316-321). In these studies, the I.H.S. was operatively used to distinguish migraine headaches from all other types of head and neck pain syndromes.

Sinusitis related headaches and pain is distinctly different than primary headaches, such as migraine and tension headaches, because of the demonstrable evidence of sinus disease. Because of the presence of associative pathology within the sinuses, sinus related head pains are examples of secondary headache syndromes, and receive unique classification under the I.H.S. and World Health Organization diagnostic systems. Under the I.H.S., diagnostic system, sinus headache is categorized as 11.5.1 (Acute sinus headache). The diagnostic operational criteria under this system is as follows:

A. Purulent or mucous discharge in the nasal passage, either by suction or spontaneous.
B. Pathologic findings in one or more of the following tests:
  1. Radiologic exam.
  2. CT/MRI.
  3. Transillumination.
C. Simultaneous onset of headache and sinusitis.
D. Headache location:
  1. In acute frontal sinusitis, headache directly over the sinus, or to the vertex, or behind the eye.
  2. In acute maxillary sinusitis, headache is located over the antral area and may radiate to the upper teeth and forehead.
  3. In ethmoidal sinusitis, the headache is located between and behind the eyes and radiates to the temporal area.
  4. In acute sphenoiditis, headache is located in the occipital area, the vertex, the frontal region, or behind the eye.
E. Headache disappears after the treatment of acute sinusitis.

Chronic sinusitis under the I.H.S. criteria is considered to be multiple relapses of acute sinusitis. Additionally, the World Health Organization code and diagnosis for sinus related head and neck pain is G44.845 (Headache associated with disease of the respiratory system) JO1 (Acute sinusitis headache) and J32 (Chronic sinusitis).

TABLE 1

Outline of International Headache Society Classification of Headache Syndromes

| | | | |
|---|---|---|---|
| 1. | Migraine | 1.5 | Childhood syndromes that |
| 1.1 | Migraine without aura | | may be precursors to or associated |
| 1.2 | Migraine with aura | | with migraine |
| 1.2.1 | Migraine with typical aura | 1.5.1 | Benign parcxysnal vertigo of |
| 1.2.2 | Migraine with prolonged aura | | childhood |
| 1.2.3 | Familial hemiplegic migraine | 1.5.2 | Alternating hemiplegia of |
| 1.2.4 | Basilar migraine | | childhood |
| 1.2.5 | Migraine aura without headache | 1.6 | Complications of migraine |
| | | 1.6.1 | Status migrainous |
| 1.2.6 | Migraine with acute onset aura | 1.6.2 | Migrainous interaction |
| | | 1.7 | Migrainous disorder not fulfilling |
| 1.3 | Ophthalmoplegic migraine | | above criteria |
| 1.4 | Retinal migraine | 2. | Tension-type Headache |
| 2.1.1 | Episodic tension-type headache associated with disorder of pericranial muscles | 2.1 | Episodic tension-type headache |
| | | 4.4 | Benign cough headache |
| | | 4.5 | Benign exertional headache |
| | | 4.6 | Headaches associated with sexual activity |
| 2.1.2 | Episodic tension-type headache unassociated with | 4.6.1 | Dull type |

TABLE 1-continued

Outline of International Headache Society Classification of Headache Syndromes

| | | | |
|---|---|---|---|
| | disorder of pericranial muscles | 4.6.2 | Explosive type |
| 2.2 | Chronic tension-type headache | 4.6.3 | Postural type |
| 2.2.1 | Chronic tension-type headache associated with disorder of pericranial muscles | 5. | Headache associated with head trauma |
| | | 5.1 | Acute posttraumatic headache |
| | | 5.1.1 | With significant head trauma and/or confirmatory signs |
| 2.2.2 | Chronic tension-type headache with disorder of pericranial muscles | 5.1.2 | With minor head trauma and no confirmatory signs |
| | | 5.2 | Chronic posttraumatic headache |
| 2.3 | Headache of the tension-type fulfilling above criteria | 5.2.1 | With significant head trauma and/or confirmatory signs |
| 3. | Cluster headache and chronic paroxysmal hemicrania | 5.2.2 | With minor head trauma and no confirmatory signs |
| 3.1 | Cluster headache | 6. | Headache associated with vascular vascular disorders |
| 3.1.1 | Cluster headache periodicity undetermined | 6.1 | Acute ischemia cerebrovascular disease |
| 3.1.2 | Episodic cluster headache | | |
| 3.1.3 | Chronic cluster headache | 6.1.1 | Transient ischemic attack (T/A) |
| 3.1.3.1 | from onset | 6.1.2 | Thromboembolic stroke |
| 3.1.3.2 | Evolved from episodic | 6.2 | Intracranial hematoma |
| 3.2 | Chronic paroxysmal hemicrania | 6.2.1 | Intracerebral hamatoma |
| 3.3 | Cluster headache-like disorder not fulfilling above criteria | 6.2.2 | Subdural hematoma |
| | | 6.2.3 | Epidural hematoma |
| 4. | Miscellaneous headaches unassociated with structural lesion | 6.3 | Superachnoid hemorrhage |
| | | 6.4 | Unruptured vascular malformation |
| 4.1 | Idiopathic stabbing headache | 6.4.1 | Arteriovenous malformation |
| 4.2 | External compression headache | 6.4.2 | Saccular aneurysm |
| 4.3 | Chronic stimulus headache | 7.5 1 | Direct effect |
| 4.3.1 | External application of a cold stimulus | 7.5.2 | Due to chemical meningitis |
| | | 7.6 | Intracrania neoplasm |
| 4.3.2 | Ingression of a cold stimulus | 7.7 | Headache associated with other intracrania disorder |
| 6.5 | Arteritis | | |
| 6.5.1 | Giant cell arteritis | 8. | Headache associated with substances or their withdrawal |
| 6.5.2 | Other systematic_ | | |
| 6.5.3 | Primary intracranial arteritis | 8.1 | Headache induced by acute substance use or exposure |
| 6.6 | Carotid or vertebral artery pain | | |
| 6.6.1 | Carotid or vertebral dissection | 8.1.1 | Nitrate incurred headache |
| 6.6.2 | Carcidynia (idiopathic) | 8.1.2 | Monosodium glutamate induced headache |
| 6.6.3 | Post endarterectomy headache | | |
| 6.7 | Various thrombosis | 8.1.3 | Carbon monoxide induced headache |
| 6.8 | Arterial hypertension | | |
| 6.8.1 | Acute pressor response to exogenous agent | 8.1.4 | Alcohol-induced headache |
| | | 8.1.5 | Other substances |
| 6.8.2 | Pheochromocytoma | 8.2 | Headache induced by chronic substance use or exposure |
| 6.8.3 | Malignant (accelerated) hypertension | | |
| | | 8.2.1 | Ergotamine induced headache |
| 6.8.4 | Preeclampsia and eclampsia | 8.2.2 | Analgesics abuse headache |
| 6.9 | Headache associated with other vascular disorder | 8.2.3 | Other substances |
| | | 8.3 | Headache from substance withdrawal (acute use) |
| 7. | Headache associated with nonvascular intracranial disorder | | |
| | | 8.3.1 | Alcohol withdrawal headache (hangover) |
| 7.1 | High cerebrospinal fluid pressure | | |
| 7.1.1 | Benign intracranial hypertension | 8.3.2 | Other substances |
| | | 8.4 | Headache from substance withdrawal (chronic use) |
| 7.1.2 | High-pressure hydrocephalus | | |
| 7.2 | Low cerebrospinal fluid pressure | 8.4.1 | Ergotamine withdrawal headache |
| 7.2.1 | Postlumbar puncture headache | | |
| 7.2.2 | Cerebrospinal fluid fistula headache | 8.4.2 | Caffeine withdrawal headache |
| | | 8.4.3 | Narcotic substance headache |
| 7.3 | Intracranial infection | 8.4.4 | Other substances |
| 7.4 | Intracranial sarcodosus and other non-infectious inflammatory diseases | 11.2.1 | Cervical spine |
| | | 11.2.2 | Retropharyngoal tendonitis |
| 7.5 | Headache related to intrathecal injections | 11.3 | Eyes |
| | | 11.3.1 | Acute glaucoma |
| | | 11.3.2 | Retractive errors |
| 8.5 | Headache associated with substances but with uncertain mechanism | 11.3.3 | Heterophonia or heterotropia |
| | | 11.4 | Eears |
| 8.5.1 | Birth control pills or estrogens | 11.5 | Nose and sinuses |
| 8.5.2 | Other substances | 11.5.1 | Acute sinus headache |
| 9. | Headache associated with noncephalic infection | 11.5.2 | Other diseases of nose or sinuses |
| 9.1 | Viral infection | 11.6 | Teeth, jaws and related structures |
| 9.1.1 | Focal noncephalic | 11.7 | Temporomandibular joint disease (functional disorders are coded to group 2) |
| 9.1.2 | Systemic | | |
| 9.2 | Bacterial infection | | |
| 9.2.1 | Focal noncephalic | 12. | Cranial neuralgias, nerve trunk pain, and dealterentation pain |
| 9.2.2 | Systemic (septicemia) | | |

TABLE 1-continued

Outline of International Headache Society Classification of Headache Syndromes

| | | | |
|---|---|---|---|
| 10. | Headache associated with metabolic disorder | 12.1 | Persistent (in contrast to tic-like) pain of cranial nerve origin |
| 10.1 | Hypoxia | 12.1.1 | Compression or distortion of cranial nerves and second or third cervical roots |
| 10.1.1 | High-altitude headache | | |
| 10.1.2 | Hypoxic headache (low-pressure environement, pulmonary disease causing hypoxia) | 12.1.2 | Demyelination of cranial nerves |
| | | 12.1.2.1 | Optic neuritis (retrobulbar neuritis) |
| 10.1.3 | Sleep apnea headache | | |
| 10.2 | Hypercapnia | 12.1.3 | In of cranial nerves |
| 10.3 | Mixed hypoxia and hypercapnia | 12.1.3.1 | Diabetic neuritis |
| 10.4 | Hypoglycemia | 12.1.4 | Inflammation of cranial nerves |
| 10.5 | Dialysis | | |
| 10.6 | Headache related to other metabolic abnormality | 12.1.4.1 | Herpes zoster |
| | | 12.1.4.2 | Chronic post-therapeutic neuralgia |
| 11. | Headache or facial pain associated with disorder of cranium, neck, eyes, ears, nose, sinuses, teeth, mouth or other facial or cranial structures | | |
| 11.1 | Cranial bone | | |
| 11.2 | Neck | | |
| 12.1.5 | Tolosa-Hunt syndrome | | |
| 12.1.6 | Neck-tongue syndrome | | |
| 12.1.7 | Other causes of persistent pain of cranial nerve origin | | |
| 12.2 | Trigeminal neuralgia | | |
| 12.2.1 | Idiopathic ingeminal neuralgia | | |
| 12.2.2 | Symptomatic ingeminal neuralgia | | |
| 12.2.2.1 | Compression of trigeminal root or ganglion | | |
| 12.2.2.2 | Central lesions | | |
| 12.3 | Glossopharyngeal neuralgia | | |
| 12.3.1 | Idiopathic glossopharyngeal neuralgia | | |
| 12.3.2 | Symptomatic glossopharyngeal neuralgia | | |
| 12.4 | Nervus intermedius neuralgia | | |
| 12.5 | Superior laryngeal neuralgia | | |
| 12.6 | Ocoptical neuralgia | | |
| 12.7 | Central causes of head and facial pain other than tic | | |
| 12.7.1 | Anaesthesia colorose | | |
| 12.7.2 | Thalamic pain | | |
| 12.8 | Facial pain not fulfilling criteria in groups 11 and 12 | | |
| 13. | Headache not classifiable | | |

D. Botulinum Toxin

Figure 2:
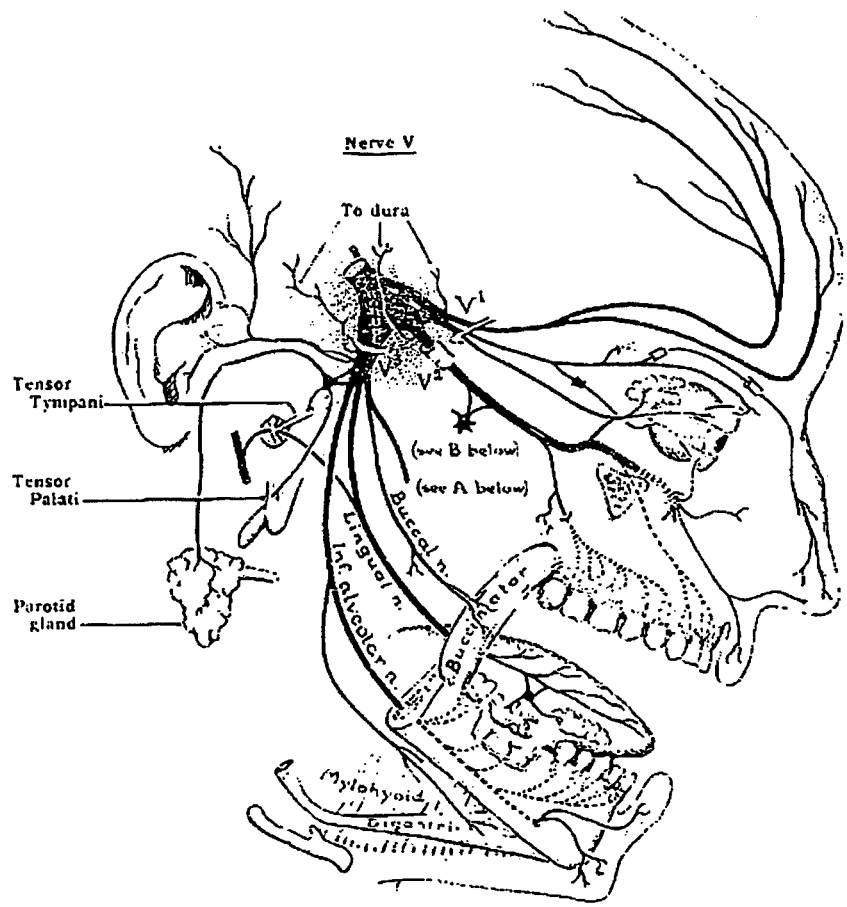
FIG. 2 shows the major divisions and branches of the trigeminal nerve.

Treatment of headache and facial pain associated with recurrent or chronic sinusitis according to the methods of the present invention may be practiced by administering botulinum toxin at a biologic activity dose ranging from 0.25-50,000 mouse $LD_{50}$ units. Although one of ordinary skill evaluates dosing of the botulinum toxin based on several factors, including patient-specific factors, the proper dosing, depending on the composition and botulinum toxin immunotype, may be determined by using a regional denervation bioassay. Preferably, a composition comprising botulinum toxin is administered at multiple sites along any dermatome, corresponding and sharing sensory innervations with a paranasal sinus (see FIGS. 1 and 2) FIG. 1 shows the trigeminal dermatomes. Note that V1 corresponds to projected sensory areas of the frontal and ethmoid sinuses. V2 corresponds to the maxillary, sphenoid, and mastoid sinuses. V3 corresponds to the maxillary sinus. FIG. 2 shows the projection of the trigeminal nerve both to the sinuses and the cutaneous and soft tissue structures of the face. Note that the opthalmic division of the trigeminal nerve projects into the frontal and ethmoid sinuses. The maxillary division and small portions of the mandibular division project into the maxillary sinuses. Sphenoid and mastoid sinuses also receive sensory innervation in part from the trigeminal nerve.

Administration of a composition comprising botulinum toxin by injection, according to the methods of the present invention, is accomplished without directly injecting the zygomatic minor and major muscles to avoid distortion of the lower face from the muscular effects of botulinum toxin.

The methods of the present invention may be practiced with any one or more botulinum toxin immunotypes. The present invention also contemplates the use of compositions comprising botulinum toxin and sequestration agents such as albumin which are disclosed in U.S. patent application Ser. No. 10/740,755, filed on Dec. 22, 2003, which is incorporated herein by reference, in its entirety.

EXAMPLES

The following Example serves to further illustrate the present invention and is not to be construed as limiting its scope in any way.

Example 1

RR is a 43-year-old man who suffered from repeated bouts of sinusitis. Radiologic studies revealed sinusitis. Treatment with decongestant and corticosteroid-type anti-inflammatory medications did not produce a sustained beneficial effect. Decompressive surgery via Culdwell-Luc approach for decompression and sinus drainage failed to produce symptomatic relief. The headaches progressed to be incapacitating. The patient had no prior history of migraine or tension (muscle contraction) headaches. Pain was experienced within the mid-face radiating and involving the temporal regions. Botulinum toxin, injected over multiple points with a 30-gauge needle, produced substantial improvement and reduction in pain, allowing the patient to return to his daily activities.

Example 2

JC is a 36-year-old woman with a history of chronic headache and face pain associated with sinus surgery. Treatment with oral analgesics and decongestants failed to produce any beneficial effects. She underwent decompressive sinus surgery months before the evaluation without pain relief. Conventional oral pain medications were ineffective. Multiple botulinum injections to the malar region and forehead at multiple sites produced over an 80% reduction in pain that was sustained for least three months. There was no past history of migraine, muscle contraction headaches, or trigeminal neuralgia. There was a history of recurrent allergies.

Example 3

JI is a 40-year-old with headache associated with recurrent sinusitis. MRI confirmed evidence of sinus mucosal edema and nasal exam showed excessive mucus and purulent secretions. The patient had no prior history of migraine or tension (muscle contraction) headaches. Conventional pain medications (decongestants, antibiotics, and anti-inflammatory nasal sprays) were not effective in relieving pain. Multiple injections of botulinum toxin were administered to soft tissues covering the maxillary, frontal and ethmoidal sinuses, resulting in at least a 50% reduction in pain.

Example 4

WR is a 38-year-old court clerk, referred for severe bifrontal headaches associated with maxillary sinusitis demonstrated on radiographic evaluations. External sinus surgery was performed without relief of the headaches. Most of the pain was localized to the left maxillary sinus region, which was tender to palpation. No past history of muscle contraction headache or migraine were identified.

Multiple injections of botulinum toxin over the sinus region, and away from the surgical incisions sites, relieved 80% of the pain. She has remained responsive for at least three years, using repeated injections of type A botulinum toxin.

Example 5

Fifteen patients with severe sinus-related headaches were evaluated in this open label trial. Each patient underwent either magnetic resonance imaging or computerized tomography of the sinus cavities that showed fluid levels, mucosal thickening, or mucous accumulation. All but one patient underwent generalized anesthesia and decompression via endoscopic osteotomies, or externally via Culdwell-Luc or frontal sinus approach. Many (>30%) underwent multiple surgical procedures to drain and decompress the sinus cavities. The duration of disease ranged from 2-9 years with an average of 3.9 years. Age of the patients ranged from 29-90 years. 8 patients were female and 7 male. Total dose per botulinum toxin injection cycles ranged from 25 to 90 international units, with an average of 49 IU. Injections were made over the soft tissues of the involved sinuses in multiple locations as well as the corresponding dermatome (see FIGS. 1 and 2). In this group, only botulinum immunotype A was used. Follow-up visits were generally made at 3 and 12 weeks. Booster injections were given if no initial response on first injection cycle was achieved. Response to injections was determined on week 12.

Of 15 patients treated, 12 patients benefited from the therapy (80%). A beneficial response was considered to be a positive response to the question: "Have you experienced at least a 50% reduction in the severity or frequency of the pain." Complications were related mainly to weakness created by the botulinum toxin injections, which caused drooping of the mouth or asymmetric smile. No side effects were permanent. Duration of benefit was approximately 12 weeks for most patients, consistent with the known duration of benefit for botulinum toxin for other uses.

We claim:

1. A method of treating headache and facial pain associated with acute recurrent or chronic sinusitis comprising the steps of selecting a subject suffering from acute recurrent or chronic sinusitis who no longer exhibits sinus inflammation, and administering a therapeutically effective amount of a composition comprising botulinum toxin to the subject's nasal mucosa or to the subcutaneous structures overlying the subject's sinuses; wherein the administration of the composition reduces the headache and facial pain associated with acute recurrent or chronic sinusitis.

2. The method of claim 1, wherein the sinuses are one or more of the sinuses selected from the group consisting of: ethmoid; maxillary; mastoid; frontal; and sphenoid.

3. The method of claim 2, wherein the subcutaneous structures overlying the sinuses lie within one or more of the areas selected from the group consisting of forehead; malar; temporal; post auricular; and lip.

4. The method of claim 1, wherein the subcutaneous structures overlying the sinuses lie within one or more of the areas selected from the group consisting of forehead; malar; temporal; post auricular; and lip.

5. The method of claim 1, wherein the composition is administered to the nasal mucosa.

6. The method of claim 1, wherein the composition is administered at a dose between 15 and 200 mouse LD50 units of botulinum toxin.

7. The method of claim 1, wherein the composition is administered at a dose between 15 and 50,000 mouse LD50 units of botulinum toxin.

8. The method of claim 1, wherein the botulinum toxin is immunotype A.

9. The method of claim 2, wherein the botulinum toxin is immunotype A.

10. The method of claim 4, wherein the botulinum toxin is immunotype A.

11. The method of claim 3, wherein the botulinum toxin is immunotype A.

12. The method of claim 1, wherein the composition is administered by injection.

13. The method of claim 12, wherein there are at least two injection sites.

14. The method of claim 2, wherein the composition is administered by injection.

15. The method of claim 14, wherein there are at least two injection sites.

16. The method of claim 4, wherein the composition is administered by injection.

17. The method of claim 16, wherein there are at least two injection sites.

18. The method of claim 3, wherein the composition is administered by injection.

19. The method of claim 18, wherein there are at least two injection sites.

20. The method of claim 1, wherein the composition is administered to the projections of the trigeminal nerve innervating the sinus.

21. The method of claim 2, wherein the composition is administered to the projections of the trigeminal nerve innervating the sinus.

22. The method of claim 4, wherein the composition is administered to the projections of the trigeminal nerve innervating the sinus.

23. The method of claim 3, wherein the composition is administered to the projections of the trigeminal nerve innervating the sinus.

24. The method of claim 12, wherein the composition is administered to the projections of the trigeminal nerve innervating the sinus.

25. The method of claim 14, wherein the composition is administered to the projections of the trigeminal nerve innervating the sinus.

26. The method of claim 16, wherein the composition is administered to the projections of the trigeminal nerve innervating the sinus.

27. The method of claim 18, wherein the composition is administered to the projections of the trigeminal nerve innervating the sinus.

28. The method of claim 13, wherein the composition is administered to the projections of the trigeminal nerve innervating the sinus.

29. The method of claim 15, wherein the composition is administered to the projections of the trigeminal nerve innervating the sinus.

30. The method of claim 17, wherein the composition is administered to the projections of the trigeminal nerve innervating the sinus.

31. The method of claim 19, wherein the composition is administered to the projections of the trigeminal nerve innervating the sinus.

32. A method of treating headache and facial pain associated with acute recurrent or chronic sinusitis comprising the steps of selecting a subject suffering from acute recurrent or chronic sinusitis who no longer exhibits sinus inflammation, and administering a therapeutically effective amount of a composition comprising botulinum toxin to a location on or within the head of the subject; wherein the administration of the composition reduces the headache and facial pain associated with acute recurrent or chronic sinusitis.

* * * * *